United States Patent
Hauer et al.

(10) Patent No.: US 6,432,685 B1
(45) Date of Patent: Aug. 13, 2002

(54) METHOD FOR THE OXIDATION OF SUBSTITUTED TRIMETHYLCYCLOHEXENYL COMPOUNDS WITH BACTERIA OF THE FAMILY STREPTOMYCETACEAE

(75) Inventors: Bernhard Hauer, Fussgönheim; Wolfgang Wohlleben, Tübingen; Peter Fischer, Stuttgart; Sabine Lutz-Wahl, Stuttgart; Claudia Schmidt-Dannert, Stuttgart; Rolf D. Schmid, Stuttgart; Oliver Scherr, Bietigheim-Bissingen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/673,149

(22) PCT Filed: Apr. 13, 1999

(86) PCT No.: PCT/EP99/02467
§ 371 (c)(1),
(2), (4) Date: Oct. 11, 2000

(87) PCT Pub. No.: WO99/55897
PCT Pub. Date: Nov. 4, 1999

(30) Foreign Application Priority Data

Apr. 27, 1998 (DE) .......................... 198 18 665

(51) Int. Cl.$^7$ .............. C12P 7/04; C12P 7/02; C12P 1/04; C12P 1/00
(52) U.S. Cl. ............ 435/157; 435/155; 435/170; 435/41
(58) Field of Search ............ 260/562, 247.2, 260/268, 293.77, 326.3, 239; 424/248, 250, 253, 320, 316; 435/41, 170, 132, 155, 157

(56) References Cited

U.S. PATENT DOCUMENTS 4,311,860 A   1/1982   Krasnobajew ............... 568/378
6,087,152 A   7/2000   Hohmann et al. ...... 435/252.31

FOREIGN PATENT DOCUMENTS

DE   3243091       5/1984
FR   2 661 190    10/1991

OTHER PUBLICATIONS

Apl.Env.Micr, Mar., 1981, 610–617, Mikami et al.
Apl.Env.Micr, Oct. 1988, 2354–2360, Yamazaki et al.
Apl.Micr.Bio.,1995 43:222–227, Larroche et al.
Microbial Carotenoids, Goodwin, 75–78,Handbook of Microbiology.
Appl. Env.Micr. vol. 64, Oct. 1998, No. 10,3878–3881, Lutz–Wahl et al.
Brock et al. Biology of Microorganisms; 6th Ed. Simon & Schuster, Englewood Cliffs, NJ. pp. 783, 1991.*

* cited by examiner

*Primary Examiner*—Jon P. Weber
*Assistant Examiner*—Patricia Patten
(74) *Attorney, Agent, or Firm*—Keil & Weinkauf

(57) ABSTRACT

The invention relates to a process for the oxidation of substituted trimethylcyclohexenyl compounds in the presence of microorganisms of the order Actinomycetales and to the use of microorganisms in oxidation reactions.

8 Claims, No Drawings

METHOD FOR THE OXIDATION OF SUBSTITUTED TRIMETHYLCYCLOHEXENYL COMPOUNDS WITH BACTERIA OF THE FAMILY STREPTOMYCETACEAE

The invention relates to a process for the oxidation of substituted trimethylcyclohexenyl compounds in the presence of microorganisms of the order Actinomycetales and to the use of microorganisms in oxidation reactions.

Compounds having a trimethylcyclohexenyl ring occur widely in nature. They are important intermediates in the terpenoid metabolism and occur, for example, during carotinoid biosynthesis. They can be isolated from a series of natural sources. For example, in addition to the carotinoids, a large number of fragrances and/or flavorings have a trimethylcyclohexenyl ring. They are also found in a large number of vegetable oils.

There have been a variety of attempts in the past at the biotechnological oxidation of compounds having a trimethylcyclohexenyl ring. Thus, Mikami et al. (Appl. Environ. Microbiol., Vol. 41, No. 3, 1981: 610–617) describes the microbial transformation of β-ionone and β-methylionone by the fungus Aspergillus niger. The main products of the reaction with β-ionone as starting material were identified as (R)-4-hydroxy-β-ionone and (S)-2-hydroxy-β-ionone, and also 2-oxo-, 4-oxo-, 3,4-dehydro-, 2,3-dehydro-4-oxo-, 3,4-dehydro-2-oxo-, (S)-2-acetoxy-, (R)-4-acetoxy-, 5,6-epoxy-β-ionone and 4-(2,3,6-trimethylphenyl)but-3-en-2-one. Analogous transformation products were identified with β-methylionone as starting material. A reaction with such a large number of secondary products is unsuitable for industrial purposes.

DE 32 43 091 describes the oxidation of β-ionone to (R)-4-hydroxy-β-ionone by the fungus Gongronella butleri. In this reaction, the principal secondary product formed is 2-hydroxy-β-ionone, which is hydroxylated in the 2-position and an undesired product.

A reaction which is an improvement on Mikami et al. is described by Yamazaki et al. (Appl. Environ. Microbiol., Vol. 54, No. 10, 1988: 2354–2360). Yamazaki uses the fungus Aspergillus niger JTS 191 as catalyst for the reaction. The main products described are a cis/trans isomer mixture (=cis-3-hydroxy-α-ionone and trans-3-hydroxy-α-ionone), together with 3-oxo-α-ionone. Other secondary products which were identified are 2,3-dehydro-α-ionone, 3,4-dehydro-α-ionone and 1-(6,6-dimethyl-2-methylene-3-cyclohexenyl)buten-3-one. Again, this process cannot be exploited industrially due to the spectrum of main and secondary products, specifically due to the cis/trans isomer mixture. Nor does the process described in FR 2 661 190, in which the fungus Mucor is employed, lead to satisfactory results.

In 1995, a fed-batch biotransformation of β-ionone using Aspergillus niger was described by Larroche et (Appl. Microbiol. Biotechnol., 43, 1995: 222–227). This biotransformation not only yields 4-hydroxy-β-ionone, but also 2-hydroxy-β-ionone and 4-oxo-β-ionone, both of which are undesired.

Our own work with a variety of fungi as catalysts has demonstrated that the oxidation of compounds having a trimethylcyclohexenyl ring leads to a multiplicity of main and secondary products.

It is an object of the present invention to provide a process for the oxidation of compounds having trimethylcyclohexenyl rings which does not exhibit the above-mentioned disadvantages and which selectively leads to oxidation products.

We have found that this object is achieved by the process according to the invention for the oxidation of compounds of the structure I

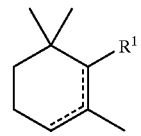

(I)

to compounds of the structure II

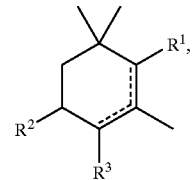

(II)

the substituents in formulae I and II being as defined below:
  $R^1$=substituted or unsubstituted, branched or unbranched, saturated or unsaturated $C_1$–$C_8$-Alkyl-,
  $R^2$ and $R^3$ independently of one another are hydrogen, oxo- or hydroxyl-, at least one radical $R^2$ or $R^3$ being other than hydrogen,
which comprises carrying out the oxidation of the compounds of the structure I in the presence of bacteria of the order Actinomycetales.

It is preferred to use the process according to the invention for oxidizing compounds of the structure Ia

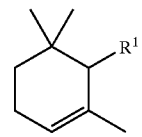

(Ia)

to compounds of the structure IIa

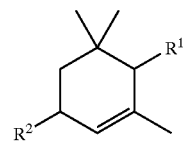

(IIa)

in the presence of bacteria of the order Actinomycetales, the substitutent $R^1$ in formulae I and IIa being as defined above and $R^2$ being oxo- or hydroxyl-.

In the compounds of the formulae I, Ia, II and IIa, $R^1$ denotes substituted, or unsubstituted, branched or unbranched, saturated or unsaturated $C_1$–$C_8$-alkyl-.

Saturated alkyl radicals which may be mentioned are substituted or unsubstituted branched or unbranched $C_1$–$C_8$-alkyl chains, such as, for example, methyl, ethyl, n-propyl, 1-methylethyl, n-butyl, 1-methylpropyl-, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl or n-octyl.

Unsaturated alkyl radicals which may be [lacuna] are subsituted or unsubstituted, branched or unbranched $C_2$–$C_8$-alkenyl chains, such as, for example, ethenyl, propenyl, 1-butenyl, 2-butenyl, 3-butenyl, 2-methylpropenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl or 7-octenyl, Other unsaturated alkyl radicals which may be [lacuna] are substituted or unsubstituted, branched or unbranched $C_2$–$C_6$-alkynyl chains, such as, for example, ethynyl-, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl.

Suitable substituents for the above-mentioned radicals of $R^1$ are, in principle, all conceivable consistuents, for example one or more substituents such as oxo, acyl-, $CHR^4OR^5$— (=acetal), halogen such as fluorine, chlorine or bromine, cyano, nitro, amino, hydroxyl, alkyl, cycloalkyl, aryl, alkoxy, benzyloxy, phenyl or benzyl, preferably oxo, hydroxyl-, acyl- or $CHR^4OR^5$— (=acetal), alkyl and cycloalkyl. $R^4$ and $R^5$ in the radicals independently of one another denote $C_1$–$C_4$-Alkyl- or $C_3$–$C_8$-cycloalkyl-.

Polyunsaturated substituted or unsubstituted, branched or unbranched $C_2$–$C_8$-alkyl chains may advantageously also be present as radicals $R^1$ in formulae I, Ia, II or IIa. The chain may contain a plurality of double bonds in conjugated or non-conjugated form, or double bonds and triple bonds may simultaneously exist in the chain. The preferred radicals 3-methyl-1,4-dipenten-1-yl- or 3-methylpent-1-yn-4-en-(5)-yl- may be mentioned by way of example.

Other preferred radicals $R^1$ which may be mentioned are radicals such as ethynyl-, hydroxymethyl-, formyl-, 3-methyl-3-hydroxy-1,4-dipenten-1-yl- or 3-hydroxy-3-methylpent-1-yn-4-en-5-yl-.

$R^2$ and $R^3$ [sic] in the compounds of the formulae II and IIa independently of one another denote hydrogen, oxo or hydroxyl-, at least one radical $R^2$ or $R^3$ being other than hydrogen and $R^2$ in formula IIa not being hydrogen. Oxo is always an oxygen bonded via a double bond.

The compounds of the structures I, Ia, II and IIa contain a double bond which may exist in two positions: either in the 4- or in the 5- position of the cyclohexane ring.

In principle, all bacteria of the order Actinomycetales are suitable for the process according to the invention. Bacteria of this order, of which the formation of branched filaments is typical, are Gram-positive. Like all suitable microorganisms, these bacteria can be isolated readily by methods known to those skilled in the art, for example from soil, compost or water samples, or obtained from culture collections like the ATCC or DSMZ. Methods for isolating these bacteria can be found, for example, in the textbooks The Prokaryotes (Eds. Mortimer T. Starr, Heinz Stolp, Hans G. Trüper, Albert Balows, Hans G. Schlegel, Springer Verlag, 1981, 2nd Edition, Chapter 147, ISBN 3-540-08871-7) or Mikrobiologisches Praktikum [Experiments in Microbiology] (Eds. [sic] Drews, 3rd Edition, Springer Verlag, 1976, pages 47 and 48). Bacteria for the process according to the invention are preferably selected from the group consisting of Nocardia, Rhodococcus, Mycobacterium, Micrococcus, Proactinomyces and of the family Streptomycetaceae of the genera Streptomyces, Streptoverticillium, Chainia, Microellobosporia and Kitasatoa.

Preferably, bacteria of the family Streptomycetaceae with the genera Streptomyces, Streptoverticillium, Chainia, Microellobosporia and Kitasatoa are used in the process according to the invention, especially preferably bacteria of the genus Streptomyces. Bacteria of genus and species such as *Streptomyces arenae, Streptomyces antibioticus, Streptomyces griseus, Streptomyces violaceoniger, Streptomyces exfoliatus, Streptomyces griseoviridis, Streptomyces fradiae, Streptomyces tendae* or *Streptomyces hygroscopicus* are very especially preferably used.

The multiplicity of the bacteria which are suitable for the reaction reflects the highly eventful history of taxa of the order Actionomycetales [sic]. The taxonomic position of the organisms mentioned has recently undergone a radical change and is still in flux since incorrect names of genera and species are being corrected and new genera are being assigned to existing strains. Close relationships exist within these genera and species. Bacteria which perform the process according to the invention are very likely to be found amongst the above-mentioned microorganisms. For example, 215 bacteria of the preferred genus Streptomyces were tested for the reaction according to the invention. 15 of these organisms performed the reaction. 15 of these organisms oxidized the specific substrate β-ionone, and 6 of these organisms were also capable of oxidizing α-ionone. This means that approximately 6% of the bacteria tested performed the desired reaction of β-ionone and approximately 3% that of α-ionone. This means that those skilled in the art have a good chance (approximately 3 to 6%) of testing any microorganisms from the order Actinomycetales, specifically the genus Streptomyces, for the reaction.

Five organisms of the bacteria tested which are particularly capable of performing the reaction according to the invention have been deposited at the DSMZ under the following numbers: DSM 12134 (=*Streptomyces arena* Tü495), DSM 12133 (=*S. antibioticus* Tü46), DSM 12135

(=*S. griseus* ATCC 13273), DSM 12131 (=*S. fradiae* Tü27) and DSM 12132 (=*S. violaceoniger* Tü38).

Advantageously, bacteria are used in the process according to the invention whose productivity is already increased over that of the wild-type isolates. Such microorganisms are expediently obtained by mutating the wild-type strains which are capable of performing the biotransformation according to the invention (see scheme I).

Known microbiological techniques may be employed for generating such mutants. To trigger mutations, all customary methods may be used, such as the use of mutagenic substances, for example, nitrosoguanidine, ethyl methanesulfonate, sodium nitrite, or exposure to electromagnetic radiation such as UV, gamma or X-ray radiation. Transposable genetic elements, such as transposons or IS elements, may furthermore be used for mutagenesis. To isolate the mutants, it is possible, for example, to exploit their capability of performing this biotransformation at an increased rate (measurement by GLC analysis, see examples).

However, such organisms may also be selected in continuous culture from a population of less well adapted individuals by adding appropriately increasing starting material/product concentrations to the fresh medium.

The biotransformation of the process according to the invention can be carried out on growing cells, quiescent cells, cell extracts or purified enzymes, advantageously in the presence of natural or artificial reduction equivalent donors and/or acceptors. The reaction is preferably carried out on growing cells.

The process according to the invention for the oxidation of compounds of the formula I or Ia to compounds of the formula II or IIa is advantageously suitable for the selective oxidation of α- or β-ionones (see scheme I). In this oxidation, monooxidized products are preferentially formed. Hardly any secondary products are formed in the reaction, if at all.

Scheme I
Biotechnological oxidation reaction

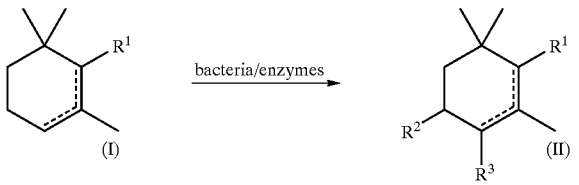

The oxidation of β-ionone in the process according to the invention preferentially yields 4-hydroxy-β-ionone, i.e. only one product, in good yields. The bacteria only form one, as yet unidentified, product in the presence of starting material (=β-ionon) and product (4-hydroxy-β-ionone) in such minute amounts that it cannot be identified analytically. It is unclear whether this compound is a secondary product of the reaction. This compound is found in amounts of ≦4%, preferably ≦2%, especially preferably ≦1%, based on the empirical parameters of GLC analysis (starting material+product; see scheme II).

Scheme II
Oxidation of β-ionone

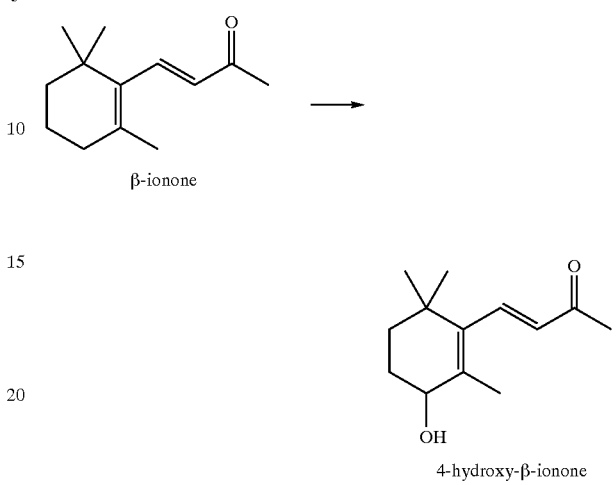

The oxidation of α-ionone in the process according to the invention preferentially yields 3-hydroxy-β-ionone, i.e. only one product, in good yields. The bacteria only form one, as yet unidentified, product in the presence of starting material (=α-ionone) and product (3-hydroxy-β-ionone) in such minute amounts that it cannot be identified analytically. It is unclear whether this compound is a secondary product of the reaction. This compound is found in amounts of ≦6%, preferably ≦4%, especially preferably ≦3%, very especially preferably ≦1%, based on the empirical parameters of GLC analysis (starting material+product; see scheme IIIa).

Scheme IIIa
Oxidation of α-ionone

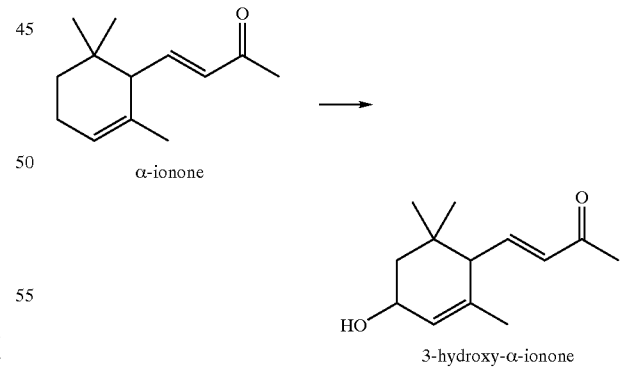

The oxidation according to the invention of compounds of the structure I or Ia advantageously leads to compounds of the structure II or IIa, in which the substituents $R^1$ and $R^2$ are in the trans-position relative to the ring plane. Thus, the process according to the invention preferentially leads to regio- and stereoselective oxidations.

Scheme IIIb
Oxidation of α-ionone to tans-isomers [sic]

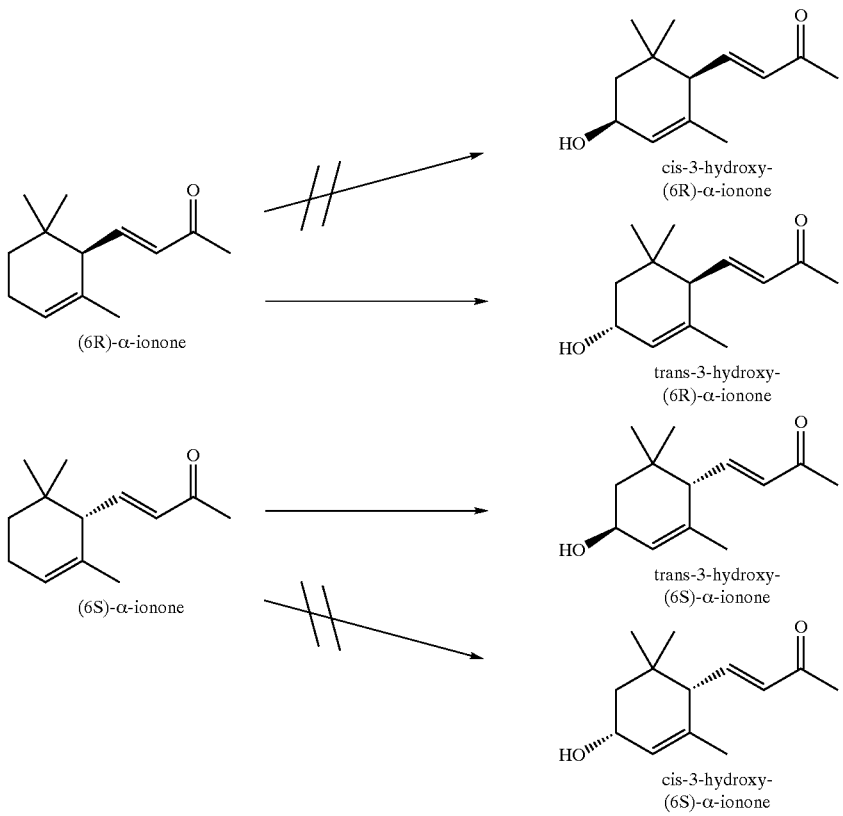

cis-3-hydroxy-
(6R)-α-ionone trans-3-hydroxy-
(6R)-α-ionone (6R)-α-ionone (6S)-α-ionone trans-3-hydroxy-
(6S)-α-ionone cis-3-hydroxy-
(6S)-α-ionone Scheme IIIb demonstrates this by way of example for the oxidation of α-ionone (=specific compound of the structure Ia) to trans-3-hydroxy-(6R)-α-ionone and/or trans-3-hydroxy-(6S)-α-ionone (=specific compounds of the structure IIa). No cis-isomers are formed.

In the process according to the invention, bacteria are grown in a medium which permits the growth of these organisms. This medium may be a synthetic or a natural medium. Depending on the organism, media known to those skilled in the art will be used. To allow microbial growth, the media used contain a carbon source, a nitrogen source, inorganic salts and, if appropriate, minor amounts of vitamins and trace elements.

Examples of advantageous carbon sources are sugars such as mono-, di- or polysaccharides such as glucose, fructose, mannose, xylose, galactose, ribose, sorbose, ribulose, lactose, maltose, sucrose, raffinose, starch or cellulose, complex sugar sources such as molasses, sugar phosphates such as fructose-1,6-bisphosphate, sugar alcohols such as mannitol, polyols such as glycerol, alcohols such as methanol or ethanol, carboxylic acids such as citric acid, lactic acid or acetic acid, fats such as soya oil or rapeseed oil, amino acids such as glutamic acid or aspartic acid or amino sugars which may simultaneously also be used as the nitrogen source.

Advantageous nitrogen sources are organic or inorganic nitrogen compounds or materials which contain these compounds. Examples are ammonium salts such as $NH_4Cl$ or $(NH_4)_2SO_4$, nitrates, urea, or complex nitrogen sources such as corn steep liquor, brewers' yeast autolysate, soybean flour, wheat gluten, yeast extract, meat extract, casein hydrolysate, yeast or potato protein, all of which can frequently also be simultaneously used as the nitrogen source.

Examples of inorganic salts are the salts of calcium, magnesium, sodium, manganese, potassium, zinc, copper and iron. Anions of these salts to be mentioned are, in particular, the chlorine [sic], sulfate and phosphate ions. An important factor for increasing the productivity in the process according to the invention is the addition of $Fe^{2+}$ or $Fe^{3+}$ salts and/or potassium salts to the production medium.

If appropriate, other growth factors are added to the nutrient medium, such as, for example, vitamins or growth promoters such as riboflavin, thiamine, folic acid, nicotinic acid, pantothenate or pyridoxine, amino acids such as alanine, cysteine, asparagine, aspartic acid, glutamine, serine, methonine [sic] or lysine, carboxylic acids such as citric acid, formic acid, pimelic acid or lactic acid, or substances such as dithiothreitol.

The fermentation of the bacteria, or the biotransformation, may be effected continuously or batchwise. As a rule, the oxidation is performed using active bacteria, but it is also successfully carried out when using quiescent bacteria, albeit at a considerably lower rate.

The mixing ratio of the nutrients mentioned depends on the type of fermentation and is decided for each individual case. All of the components of the medium may be introduced into the fermentation vessel at the beginning of the fermentation, if appropriate after having been sterilized separately or jointly, or else they may be fed continuously or batchwise during the fermentation, as required.

The culture conditions are specified in such a way that the organisms' growth is optimal and that the best possible yields are achieved. Preferred culture temperatures are at 15° C. to 40° C. Temperatures between 25° C. and 37° C. are especially advantageous. The pH is preferably maintained in a range from 3 to 9. pH values of between 5 and 8 are especially advantageous. In general, an incubation time of a few hours to several days, preferably 8 hours up to 21 days, especially preferably 4 hours to 14 days, will suffice. The maximum amount of product is concentrated in the medium within this period.

Advantageous media and growth conditions for the process according to the invention can be found, for example, in the above-mentioned textbook "The Prokaryotes" or in culture collection catalogues, such as that of the DSMZ or the ATCC.

The oxidation process according to the invention may be carried out continuously, batchwise or fed-batchwise, it being possible to introduce the starting material at the beginning of the fermentation or else add it later, continuously or batchwise. The concentration of starting material is advantageously in a range from 0.1 to 5 g/l, concentrations of 0.5 to 2 g/l being preferred. Alternatively, the starting material may be added in the form of a dilute aqueous or organic solution.

The process according to the invention leads to advantageous product yields of at least 10, preferably 20, especially preferably 30%, based on starting material employed.

The concentration of starting material is preferably controlled within a range which ensures that no growth-inhibitory concentrations of the starting material are reached. This can be determined readily for a particular starting material and a given microorganism by simple preliminary experiments with which those skilled in the art will be familiar. For example, growth curves of the organisms are recorded and the starting material concentrations at which the growth rate decreases markedly are thus analyzed.

The conversion can be monitored and checked regularly by sampling and analyzing the samples (GLC). The products may be isolated and purified from the culture liquid by known methods (see examples). Expediently, the solid biomass is separated from the nutrient medium or transformation medium, the product of interest is extracted, for example using an organic solvent, and the product of interest is isolated from the extract phase. Column chromatography methods are also expedient for work-up.

The invention is illustrated in greater detail by the examples which follow.

EXAMPLES

Three complex media and one synthetic medium were used for growing the bacteria and for the biotransformation reactions, specifically of the α- and β-ionones.

| Medium A: | |
|---|---|
| Soybean flour | 20 g/l |
| Mannitol | 20 g/l |
| pH 7.5 | |
| Medium B: | |
| Nutrient broth | 8 g/l |
| Yeast extract | 10 g/l |
| Glucose | 5 g/l |
| pH 7.0 | |

-continued

| Medium C: | |
|---|---|
| $(NH_4)_2SO_4$ | 5.0 g/l |
| $MgSO_4 \cdot 7H_2O$ | 0.5 g/l |
| $MnSO_4 \cdot H_2O$ | 0.05 g/l |
| $K_2HPO_4$ | 3.6 g/l |
| $KH_2PO_4$ | 1.5 g/l |
| Glucose | 2 g/l |
| $FeSO_4 \cdot H_2O$ | 0.2 g/l |
| $ZnSO_4 \cdot 7H_2O$ | 10 mg/l |
| $MnCl_2 \cdot 4H_2O$ | 3 mg/l |
| $H_3BO_3$ | 30 mg/l |
| $CaCl_2 \cdot 6H_2O$ | 20 mg/l |
| $CUCl_2 \cdot 2H_2O$ | 1 mg/l |
| $NiCl_2 \cdot 6H_2O$ | 2 mg/l |
| $Na_2MoO_4 \cdot 2H_2O$ | 3 mg/l |
| Titriplex III | 500 mg/l |
| pH | 7.0 |
| Medium D: | |
| Soybean flour | 15 g/l |
| NaCl | 5 g/l |
| Corn steep liquor | 5 g/l |
| $CaCl_2$ | 2 g/l |
| Glucose | 15 g/l |
| pH 7.0 | |

A variety of Streptomyces strains were tested in a first screening series for hydroxylation activity towards β-ionone as starting material. To this end, precultures of the strains were inoculated in 5 ml of medium A starting from agar slants and incubated for 2 days at 28 to 30° C. 100 ml of medium A were then inoculated with 3 ml of the preculture and incubated on a shaker at 28 to 30° C./150 rpm. After incubation for 2 days, 0.1% of β-ionone (w/v) was added to the cultures, and incubation was continued for 5 more days. The cells were then separated off by filtration, and 2-ml-aliquots of the filtrate were extracted with ethyl acetate/hexane (3:2) or diethyl ether. The extract was analyzed by thin-layer chromatography (=TLC). Analogous cultures without starting material were made and analyzed, and acted as the control. The stability of the starting material in medium A was determined under identical incubation conditions and confirmed.

Two of the Streptomyces strains which showed conversion (ATCC 13273 and Lu1537) were examined in greater detail in a second screening series for their ability of oxidizing β-ionone under the same conditions. Each day, 1-ml-aliquots were sampled, filtered and extracted as described in Example 1 and analyzed by TLC or gas liquid chromatography (=GLC). After 10 to 12 days, the cultures were worked up fully as described and analyzed. The biotransformation and work-up with α-ionone as the starting material was carried out analogously.

Larger culture volumes (for example >100 ml) were filtered and the filtrate was extracted twice with diethyl ether (50 ml). The combined extracts were washed with saturated aqueous NaCl solution and dried with $MgSO_4$ or $Na_2SO_4$, and the residue was concentrated in vacuo to a volume of 1 to 2 ml (rotary evaporator, 42° C.).

For TLC analysis, extract samples were applied to TLC plates (0.2 mmm [sic], silica 60 $F_{254}$, Merck Darmstadt) and subsequently developed with hexane/ethyl acetate (3:2). The products were detected on the basis of their fluorescence quenching at 254 nm and/or by means of spraying with 2.5% (w/v) vanillin solution in 95% $EtOH/H_2SO_4$ and subsequent heating. α- and β-ionone standards and standards of 3- and 4-hydroxy-β-ionone were also applied. A similar procedure was followed for α-ionone.

GC analysis (=GLC) was performed using a Carlo Erba MEGA 5300 gas chromatograph: split injection (1:5, 220° C.); flame ionization detector (=FID); Spectra Physics Lab-net Version 3.5 integrator system; carrier gas 0.4 bar $H_2$; 20 m glass capillary (i.th. 0.3 mm, film thickness 0.2 μm), occupied by a chiral polydimethylsiloxane phase (modified with chemically bound permethyl-α- or -β-cyclodextrin (0.38 and 0.34%, respectively); temperature program 100° C. (1 min isothermal)/100–220° C. (4°/min). The samples were applied as a solution in dichloromethane. The following conditions prevailed:

Temperature program: 100° C. (1 min isothermal)— 100–220° C. (4° C./min)

Pressure: 0.4 bar $H_2$. The samples were applied in [sic] a solution in $CH_2Cl_2$.

NMR spectra were recorded in $CDCl_3$ solutions using a Bruker (Karlsruhe-Forchheim, Germany) ARX 500 spectrometer (frequency 500.13 MHz for $^1H$ and 125.77 MHz for $^{13}C$).

Example 1

In the first experiment, 215 different Streptomycetes strains were tested for their capability of oxidizing β-ionone. Amongst the 4 different media, medium A proved to be especially suitable. TLC analysis demonstrated that 13 of the strains showed products of greater polarity. These strains were again cultured on a larger scale, and the biotransformation was monitored as described above over 10 to 12 days. The batches were then subjected to complete work-up (see above) and analyzed by GLC (see Table I). In addition to 4-hydroxy-β-ionone as the product, only one further, unidentifiable component was found (see Table I, column 4, component X).

TABLE I

Biotransformation of β-ionone

| Strains | β-ionone (%) | 4-hydroxy-β-ionone (%) | component X (%) |
| --- | --- | --- | --- |
| S. arenae Tü495 | 66 | 33 | 1 |
| S. antibioticus Tü46 | 74 | 22 | 4 |
| S. spec. Tü124 | 86 | 12 | 2 |
| S. griseus ATCC 13273 | 88 | 10 | 2 |
| S. griseus Tü18 | 88 | 10 | 2 |
| S. griseus Tü781A | 90 | 8 | 2 |
| S. griseus Tü17 | 90 | 8 | 2 |
| S. violaceoniger Tü38 | 91 | 7 | 2 |
| S. exfoliatus Tü1424 | 92 | 7 | 1 |
| S. griseoviridis Tü1963 | 92 | 6 | 2 |
| S. antibioticus Tü4 | 94 | 5 | 1 |
| S. fradiae Tü27 | 94 | 4 | 2 |
| S. griseus Tü16 | 94 | 5 | <1 |
| S. tendae Tü21 | 95 | 4 | <1 |
| S. hygroscopicus Lu1537 | 72 | <1 | 27 |

Most of the strains only exhibit low conversion rates, with the exception of S. antibioticus and S. arenae (22 and 33%, respectively). Only 4-hydroxy-β-ionone was found as product (detection: GLC and NMR). No complex product mixture as obtained with fungi such as Aspergillus niger was found.

Example 2

Biotransformation experiments on α-ionone similar to those described in Example 1 demonstrated that 6 of the strains are capable of hydroxylating α-ionone. The product identified by GLC and NMR was 3-hydroxy-α-ionone. Chiral GC revealed two product peaks, which correspond to the two trans isomers (see Scheme IIIb). Thus, hydroxylation is regioselective and stereoselective. Again, no product mixture is obtained in the case of α-ionone, in contrast to Aspergillus niger. Again, in the case of α-ionone, only one unknown secondary product (=Table II, column 4, component X) appears, with the exception of S. arenae Tü495 (2 more secondary products). The results of the experiments are shown in Table II.

TABLE II

Oxidation of α-ionone

| Strains | α-ionone (%) | 3-hydroxy-α-ionone (%) | component X (%) |
| --- | --- | --- | --- |
| S. arenae Tü495 | 35 | 54 | 2 |
| S. antibioticus Tü46 | 90 | 7 | 3 |
| S. spec. Tü124 | 94 | 0 | 6 |
| S. griseus ATCC 13273 | 49 | 50 | 1 |
| S. griseus Tü18 | 98 | 0 | 2 |
| S. griseus Tü781A | 98 | 0 | 2 |
| S. griseus Tü17 | 94 | <1 | 5 |
| S. violaceoniger Tü38 | 55 | 44 | <1 |
| S. exfoliatus Tü1424 | 97 | 0 | 3 |
| S. griseoviridis Tü1963 | 81 | 0 | 9 |
| S. antibioticus Tü4 | 68 | 28 | 4 |
| S. fradiae Tü27 | 21 | 75 | 3 |
| S. griseus Tü16 | 98 | 0 | 2 |
| S. tendae Tü21 | 79 | 0 | 21 |
| S. hygroscopicus Lu1537 | 99 | 0 | 1 |

For NMR analysis, the extraction residues were taken up in 1 ml of $CDCl_3$, dried using molecular sieve, filtered and measured. In both cases, the oxidation products were identified unambiguously by NMR as 4-hydroxy-β-ionone and 3-hydroxy-α-ionone.

We claim:

1. A process for the oxidation of compounds of the structure 1

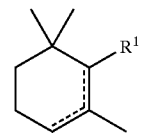

(1)

to compounds of the structure 2

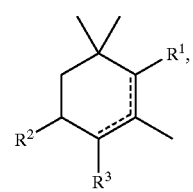

(2)

the substituents in formulae 1 and 2 being as defined below:

$R^1$=substituted or unsubstituted, branched or unbranched, saturated or unsaturated $C_1$–$C_8$-Alkyl-, $R^2$ and $R^3$ independently of one another are hydrogen, oxo- or hydroxyl-, at least one radical $R^2$ or $R^3$ being other than hydrogen, which comprises oxidizing of the compounds of structure 1 with bacteria of the family Streptomycetaceae.

2. A process as claimed in claim 1, wherein compounds of the structure 3

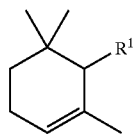

are oxidized to compounds of the structure 4

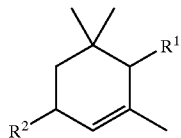

with bacteria of the family Streptomycetaceae, the substituent $R^1$ in the formulae 3 and 4 being as defined in claim 6 and $R^2$ being oxo- or hydroxyl-.

3. A process as claimed in claim 2, wherein the oxidation is performed with bacteria selected from the group consisting of the genera Streptomyces, Streptoverticillium, Chainia, Microellobosproia and Kitasatoa.

4. A process as claimed in claim 2, where in the oxidation is performed with bacteria of the genus Streptomyces.

5. A process as claimed in claim 1, wherein the product formed is a compound of the formula II or IIa whose substituents $R^1$ and $R^2$ or $R^3$ are in the trans-position relative to the ring plane.

6. A process as claimed in claim 1, wherein the oxidation is carried out with growing cells.

7. A process as claimed in claim 1, wherein the oxidation is performed with bacteria selected from the group consisting of the genera Streptomyces, Streptoverticillium, Chainia, Microellobosporia and Kitasatoa.

8. A process as claimed in claim 1, where in the oxidation is performed with bacteria of the genus Streptomyces.

* * * * *